(12) United States Patent
Shin et al.

(10) Patent No.: US 7,645,844 B2
(45) Date of Patent: Jan. 12, 2010

(54) TRANSITION METAL COMPLEXES, CATALYST COMPOSITIONS CONTAINING THE SAME, AND METHODS FOR PREPARING ETHYLENE HOMOPOLYMERS OR COPOLYMERS OF ETHYLENE AND α-OLEFINS USING THE SAME

(75) Inventors: Dong-Cheol Shin, Daejeon (KR); Ho-Seong Lee, Seoul (KR); Myung-Ahn Ok, Daejeon (KR); Jong-Sok Hahn, Daejeon (KR)

(73) Assignee: SK Energy Co., Ltd., Seoul (KR)

( * ) Notice: Subject to any disclaimer, the term of this patent is extended or adjusted under 35 U.S.C. 154(b) by 0 days.

(21) Appl. No.: 12/318,673

(22) Filed: Jan. 6, 2009

(65) Prior Publication Data

US 2009/0176949 A1 Jul. 9, 2009

(30) Foreign Application Priority Data

Jan. 7, 2008 (KR) .................. 10-2008-0001639

(51) Int. Cl.
*C08F 4/44* (2006.01)
*C08F 10/14* (2006.01)
*B01J 31/00* (2006.01)

(52) U.S. Cl. .............. 526/127; 502/155; 526/348.2; 526/348.3; 526/348.4; 526/348.5; 526/348.6; 526/943; 556/11; 556/52

(58) Field of Classification Search ............. 526/135, 526/160
See application file for complete search history.

(56) References Cited

U.S. PATENT DOCUMENTS

| | | | |
|---|---|---|---|
| 4,752,597 | A | 6/1988 | Turner |
| 5,043,408 | A | 8/1991 | Kakugo et al. |
| 5,079,205 | A | 1/1992 | Canich |
| 5,198,401 | A | 3/1993 | Turner et al. |
| 6,329,478 | B1 | 12/2001 | Katayama et al. |
| 6,967,231 | B1 | 11/2005 | Wang et al. |

| | | | |
|---|---|---|---|
| 2007/0135597 | A1* | 6/2007 | Voskoboynikov et al. ... 526/127 |

FOREIGN PATENT DOCUMENTS

| | | |
|---|---|---|
| EP | 0 320 762 | 6/1989 |
| EP | 0 372 632 | 6/1990 |
| EP | 0 416 815 | 3/1991 |
| EP | 0 420 436 | 4/1991 |
| EP | 0 842 939 | 5/1998 |
| EP | 1 013 675 | 6/2000 |
| EP | 1 195 386 | 4/2002 |
| JP | 63-92621 | 4/1988 |
| JP | 2-84405 | 3/1990 |
| JP | 3-2347 | 1/1991 |
| JP | 8-208732 | 8/1996 |
| JP | 2002-212218 | 7/2002 |
| KR | 10-2001-0074722 | 8/2001 |

OTHER PUBLICATIONS

K. Nomura et al., "Synthesis of Nonbridged (Anilide)(cyclopentadienyl)titanium(IV) Complexes of the Type Cp'TiCl$_2$[N(2,6-Me$_2$C$_6$H$_3$)(R)] and Their Use in Catalysis for Olefin Polymerization", *Organometallics* 2002, 21, 3042-3049.
Nomura, Kotohiro et al., "Nonbridged half-metallocenes containing anionic ancillary donor ligands: New promising candidates as catalysts for precise olefin polymerization" (2007) *Journal of Molecular Catalysis A: Chemical*, vol. 267, pp. 1-29.

* cited by examiner

*Primary Examiner*—James Seidleck
*Assistant Examiner*—Sonya Wright
(74) *Attorney, Agent, or Firm*—Clark & Brody

(57) ABSTRACT

The present invention relates to a transition metal complex and a transition metal catalyst composition comprising the same for the preparation of an ethylene homopolymer or a copolymer of ethylene and α-olefin. More particularly, it relates to a group IV transition metal catalyst having a cyclopentadiene derivative and at least one aryl oxide ligand in which an oxygen-containing heterocycle is fused at the ortho-position around a group IV transition metal, with no crosslinkage between the ligands, a catalyst composition comprising the transition metal catalyst and an aluminoxane cocatalyst or a boron compound cocatalyst, and a process for preparing an ethylene homopolymer or a copolymer of ethylene and α-olefin using the same.

14 Claims, No Drawings

TRANSITION METAL COMPLEXES, CATALYST COMPOSITIONS CONTAINING THE SAME, AND METHODS FOR PREPARING ETHYLENE HOMOPOLYMERS OR COPOLYMERS OF ETHYLENE AND α-OLEFINS USING THE SAME

CROSS-REFERENCE TO RELATED APPLICATION

This application claims priority under 35 U.S.C. §119 the benefit of Korean Patent Application No. 10-2008-0001639, filed on Jan. 7, 2008, the entire contents of which are incorporated herein by reference.

BACKGROUND

1. Technical Field

The present invention relates to a transition metal complex and a transition metal catalyst composition comprising the same for the preparation of an ethylene homopolymer or a copolymer of ethylene and α-olefin. More particularly, it relates to a group IV transition metal catalyst having a cyclopentadiene derivative and at least one aryl oxide ligand in which an oxygen-containing heterocycle is fused at the ortho-position around a group IV transition metal, with no crosslinkage between the ligands, a catalyst composition comprising the transition metal catalyst and an aluminoxane cocatalyst or a boron compound cocatalyst, and a process for preparing an ethylene homopolymer or a copolymer of ethylene and α-olefin using the same.

2. Description of the Related Art

Conventionally, Ziegler-Natta catalyst systems comprising titanium or vanadium compounds as main catalyst and alkylaluminum compounds as cocatalyst have been used to prepare ethylene homopolymers or copolymers of ethylene and α-olefin. Although the Ziegler-Natta catalyst system provides good efficiency of ethylene polymerization, the resulting polymers tend to have a broad molecular weight distribution because of the heterogeneousness of catalytic active sites. In particular, the compositional distribution is not uniform for a copolymer of ethylene and α-olefin.

Recently, the so-called metallocene catalyst system, which comprises metallocene compounds of group IV transition metals, e.g. titanium, zirconium or hafnium, and methylaluminoxane as cocatalyst, has been developed. Because this catalyst system is a homogeneous cocatalyst having homogeneous catalytic active sites, it is capable of preparing polyethylenes having a narrower molecular weight distribution and a more uniform compositional distribution as compared to the Ziegler-Natta catalyst system. For example, European Patent Publication Nos. 320,762 and 372,632 or Japanese Patent Laid-Open Nos. Sho 63-092621, Hei 02-84405 and Hei 03-2347 disclose that polyethylenes having a molecular weight distribution ($M_w/M_n$) of 1.5-2.0 can be prepared efficiently from ethylene by activating the metallocene compounds $Cp_2TiCl_2$, $Cp_2ZrCl_2$, $Cp_2ZrMeCl$, $Cp_2ZrMe_2$, ethylene $(IndH_4)_2ZrCl_2$, etc. with the cocatalyst methylaluminoxane. However, it is difficult to obtain high molecular weight polymers with this catalyst system. Especially, when applied to solution polymerization performed at high temperature, i.e. 140° C. or higher, it is not suitable to prepare high molecular weight polymers having a weight average molecular weight ($M_w$) of 100,000 or larger because the polymerization efficiency decreases rapidly and β-hydrogenation dominates.

Recently, the so-called geometrically constrained non-metallocene catalyst system (also known as the single-site catalyst) enabling the preparation of high molecular weight polymers through homopolymerization of ethylene or copolymerization of ethylene and α-olefin under the solution polymerization condition, in which a transition metal is connected as a ring. European Patent Publication Nos. 0416815 and 0420436 disclose a compound in which an amide group is connected to a cyclopentadiene ligand to form a ring. And, European Patent Publication No. 0842939 discloses an electron donor compound catalyst in which a phenol-based ligand and a cyclopentadiene ligand are connected to form a ring. However, the geometrically constrained catalyst is inappropriate for commercial application because the yield of the ring forming reaction between the ligand and the transition metal compound in the synthesis of the catalyst is very low.

U.S. Pat. No. 6,329,478 and Korean Patent Publication No. 2001-0074722 disclose non-geometrically constrained, non-metallocene catalysts. These patents disclose that single-site catalysts having at least one phosphinimine compound as ligand provide superior ethylene transition ratio during the copolymerization of ethylene and α-olefin by solution polymerization under high temperature condition of 140° C. or higher. U.S. Pat. No. 5,079,205 discloses a catalyst having a bisphenoxide ligand, and U.S. Pat. No. 5,043,408 discloses a catalyst having a chelate type bisphenoxide ligand. However, these catalysts have too low a catalytic activity to be commercially applicable in the preparation of an ethylene homopolymer or a copolymer of ethylene and α-olefin carried out at high temperature.

Japanese Paten Laid-Open Nos. 1996-208732 and 2002-212218 disclose a use of a catalyst for olefin polymerization having an anilido ligand. But, the patents do not state preparation in a commercially meaningful polymerization temperature range. Further, the catalyst is structurally different from the transition metal catalyst presented by the present invention having an anilido ligand with an aryl substituent at the ortho-position. In addition, although use of an anilido ligand as non-metallocene catalyst for polymerization is reported by Nomura et al. [*Organometallics* 2002, 21, 3043], the relevant substituent is simply limited methyl.

The above information disclosed in this Background section is only for enhancement of understanding of the background of the invention and therefore it may contain information that does not form the related art that is already known in this country to a person of ordinary skill in the art.

SUMMARY

The inventors of the present invention have carried out extensive researches to solve the aforesaid problems associated with the related art. As a result, they have found that a non-crosslinked transition metal catalyst having a cyclopentadiene derivative and at least one aryl oxide ligand in which an oxygen-containing heterocycle is fused at the ortho-position exhibits superior catalytic activity for the polymerization of ethylene and olefins. Based on this finding, they have developed a catalyst which can be applied in a polymerization process performed at 60° C. or higher to provide high molecular weight olefin homopolymers or copolymers of ethylene and α-olefin with good efficiency.

Accordingly, an object of the present invention is to provide a transition metal complex useful as a catalyst for preparing an ethylene homopolymer or a copolymer of ethylene and α-olefin, a catalyst composition comprising the same, and an ethylene homopolymer or a copolymer of ethylene and α-olefin prepared using the same. Another object of the present invention is to provide a single-site catalyst which can be synthesized very economically through a simple synthesis procedure and can provide excellent catalytic activity for olefin polymerization, and a process for preparing ethylene homopolymers or copolymers of ethylene and α-olefin with various physical properties using the catalyst.

In order to attain the objects, in an aspect, the present invention provides a group IV transition metal complex represented by the following Chemical Formula 1, more specifically, one having a cyclopentadiene derivative and at least one aryl oxide ligand in which an oxygen-containing heterocycle is fused at the ortho-position, with no crosslinkage between the ligands, which is useful as a catalyst in the preparation of an ethylene homopolymer or a copolymer of ethylene and α-olefin:

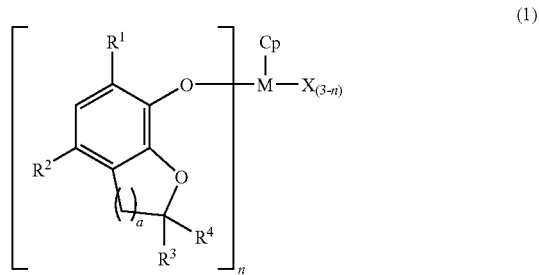

(1)

where M is a group IV transition metal; Cp is a cyclopentadienyl ring or a fused ring including a cyclopentadienyl ring which is capable of forming a $\eta^5$-bonding with M, wherein the cyclopentadienyl ring or the cyclopentadienyl fused ring may be more substituted by (C1-C20)alkyl, (C6-C30)aryl, (C2-C20)alkenyl or (C6-C30)aryl (C1-C20)alkyl; $R^1$ and $R^2$ are independently hydrogen, (C1-C20)alkyl, (C3-C20)cycloalkyl, (C6-C30)aryl, (C1-C20)alkyl (C6-C30)aryl, (C1-C20) alkyl-substituted or (C6-C30)aryl-substituted silyl, (C6-C30)aryl (C1-C10)alkyl, (C1-C20)alkoxy, (C1-C20) alkyl-substituted or (C6-C20)aryl-substituted siloxy, (C1-C20)alkyl-substituted or (C6-C30)aryl-substituted amino, (C1-C20)alkyl-substituted or (C6-C30)aryl-substituted phosphine, (C1-C20)alkyl-substituted mercapto, or nitro; $R^3$ and $R^4$ are independently hydrogen, (C1-C20)alkyl, (C3-C20)cycloalkyl, (C6-C30)aryl, (C1-C20) alkyl (C6-C30) aryl, or (C6-C30)aryl (C1-C20)alkyl; a is an integer 1 or 2; n is an integer from 1 to 3; and X independently is halogen, (C1-C20)alkyl, (C3-C20)cycloalkyl, (C6-C30)aryl (C1-C20) alkyl, (C1-C20)alkoxy, (C3-C20)alkylsiloxy, (C1-C20) alkyl-substituted or (C6-C30)aryl-substituted amino, (C1-C20)alkyl-substituted or (C6-C30)aryl-substituted phosphine, or (C1-C20)alkyl-substituted mercapto.

In another aspect, the present invention provides a transition metal catalyst composition comprising the transition metal complex and an aluminoxane cocatalyst or a boron compound cocatalyst.

In another aspect, the present invention provides a process for preparing an ethylene homopolymer or a copolymer of ethylene and α-olefin using the transition metal complex or the catalyst composition.

DETAILED DESCRIPTION OF EMBODIMENTS

Hereinafter, reference will now be made in detail to various embodiments of the present invention, examples of which are described below. While the invention will be described in conjunction with example embodiments, it will be understood that the present description is not intended to limit the invention to those example embodiments. On the contrary, the invention is intended to cover not only the example embodiments, but also various alternatives, modifications, equivalents and other embodiments, which may be included within the spirit and scope of the invention as defined in the appended claims.

In the transition metal catalyst represented by Chemical Formula 1, the group IV transition metal M is preferably titanium, zirconium or hafnium.

And, Cp is a cyclopentadienyl ring or a substituted or unsubstituted fused ring including a cyclopentadienyl ring, such as a substituted cyclopentadiene ring, an indenyl ring, a fluorenyl ring, etc., which is capable of forming a $\eta^5$-bonding with the center metal. Specific examples may include cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, fluorenyl, methylfluorenyl, dimethylfluorenyl, ethylfluorenyl, isopropylfluorenyl, etc.

The substituents $R^1$ and $R^2$ of the aryl oxide ligand are independently: hydrogen; linear or branched (C1-C20)alkyl, e.g. methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl or n-eicosyl, preferably methyl, ethyl, n-propyl, isopropyl, n-butyl or tert-butyl; linear or branched (C1-C20)alkyl-substituted or (C6-C30)aryl-substituted silyl, e.g. methylsilyl, ethylsilyl, phenylsilyl, dimethylsilyl, diethylsilyl, diphenylsilyl, trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyldimethylsilyl, tri-n-pentylsilyl, tri-n-hexylsilyl, tricyclohexylsilyl or triphenylsilyl, preferably trimethylsilyl, tert-butyldimethylsilyl or triphenylsilyl; (C6-C30)aryl or (C1-C20)alkyl (C6-C30)aryl, e.g. phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl or anthracenyl, preferably phenyl, naphthyl, biphenyl, 2-isopropylphenyl, 3,5-xylyl or 2,4,6-trimethylphenyl; (C6-C30)aryl (C1-C10) alkyl, e.g. benzyl, 2-methylphenylmethyl, 3-methylphenylmethyl, 4-methylphenylmethyl, 2,3-dimethylphenylmethyl, 2,4-dimethylphenylmethyl, 2,5-dimethylphenylmethyl, 2,6-dimethylphenylmethyl, 3,4-dimethylphenylmethyl, 4,6-dimethylphenylmethyl, 2,3,4-trimethylphenylmethyl, 2,3,5-trimethylphenylmethyl, 2,3,6-trimethylphenylmethyl, 3,4,5-trimethylphenylmethyl, 2,4,6-trimethylphenylmethyl, 2,3,4,5-tetramethylphenylmethyl, 2,3,4,6-tetramethylphenylmethyl, 2,3,5,6-tetramethylphenylmethyl, pentamethylphenylmethyl, ethylphenylmethyl, n-propylphenylmethyl, isopropylphenylmethyl, n-butylphenylmethyl, sec-butylphenylmethyl, tert-butylphenylmethyl, n-pentylphenylmethyl, neopentylphenylmethyl, n-hexylphenylmethyl, n-octylphenylmethyl, n-decylphenylmethyl, n-dodecylphenylmethyl, n-tetradecylphenylmethyl, naphthylmethyl or anthracenylmethyl, preferably benzyl; (C1-C20)alkoxy, e.g. methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy or n-eicosoxy, preferably methoxy, ethoxy, isopropoxy or tert-butoxy; (C1-C20)alkyl-substituted or (C6-C20)aryl-substituted siloxy, e.g. trimethylsiloxy, triethylsiloxy, tri-n-propylsiloxy, triisopropylsiloxy, tri-n-butylsiloxy, tri-sec-butylsiloxy, tri-tert-butylsiloxy, triisobutylsiloxy, tert-butyldimethylsiloxy, tri-n-pentylsiloxy, tri-n-hexylsiloxy tricyclohexylsiloxy or triphenylsiloxy, preferably trimethylsiloxy, tert-butyldimethylsiloxy or triphenylsiloxy; (C1-C20)alkyl-substituted or (C6-C30)aryl-substituted amino, e.g. dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bistrimethylsilylamino or bis-tert-butyldimethylsilylamino, preferably dimethylamino, diethylamino or diphenylamino; (C1-C20)alkyl-substituted or (C6-C30)aryl-substituted phosphine, e.g. dimethylphosphine, diethylphosphine, di-n-propylphosphine, diisopropylphosphine, di-n-butylphosphine, di-sec-butylphosphine, di-tert-butylphosphine, diisobutylphosphine, tert-butylisopropylphosphine, di-n-hexylphosphine, di-n-octylphosphine, di-n-decylphosphine, diphenylphosphine, dibenzylphosphine, methylethylphosphine, methylphenylphosphine, benzylhexylphosphine, bistrimethylsilylphosphine or bis-tert-butyldimethylsilylphosphine; or (C1-C20)alkyl-substituted mercapto, e.g. methylmercaptan, ethylmercaptan, propylmercaptan, isopropylmercaptan, 1-butylmercaptan or isopentylmercaptan, preferably ethylmercaptan or isopropylmercaptan; or nitro.

The substituents $R^3$ and $R^4$ are independently: hydrogen; linear or branched (C1-C20)alkyl, e.g. methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl or n-eicosyl, preferably methyl, ethyl, n-propyl, isopropyl, n-butyl or tert-butyl; (C3-C20)cycloalkyl, e.g. cyclopropyl, cyclobutyl, cyclopentyl, cyclohexyl, cycloheptyl or adamantyl, preferably cyclopentyl or cyclohexyl; (C6-C30)aryl or (C1-C20)alkyl (C6-C30)aryl, e.g. phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl or anthracenyl, preferably phenyl, naphthyl, biphenyl, 2-isopropylphenyl, 3,5-xylyl or 2,4,6-trimethylphenyl; (C6-C30)aryl (C1-C20)alkyl, e.g. benzyl, 2-methylphenylmethyl, 3-methylphenylmethyl, 4-methylphenylmethyl, 2,3-dimethylphenylmethyl, 2,4-dimethylphenylmethyl, 2,5-dimethylphenylmethyl, 2,6-dimethylphenylmethyl, 3,4-dimethylphenylmethyl, 4,6-dimethylphenylmethyl, 2,3,4-trimethylphenylmethyl, 2,3,5-trimethylphenylmethyl, 2,3,6-trimethylphenylmethyl, 3,4,5-trimethylphenylmethyl, 2,4,6-trimethylphenylmethyl, 2,3,4,5-tetramethylphenylmethyl, 2,3,4,6-tetramethylphenylmethyl, 2,3,5,6-tetramethylphenylmethyl, pentamethylphenylmethyl, ethylphenylmethyl, n-propylphenylmethyl, isopropylphenylmethyl, n-butylphenylmethyl, sec-butylphenylmethyl, tert-butylphenylmethyl, n-pentylphenylmethyl, neopentylphenylmethyl, n-hexylphenylmethyl, n-octylphenylmethyl, n-decylphenylmethyl, n-dodecylphenylmethyl, n-tetradecylphenylmethyl, naphthylmethyl or anthracenylmethyl, preferably benzyl.

X may be: halogen, e.g. fluorine, chlorine, bromine or iodine; (C1-C20)alkyl other than a cyclopentadienyl derivative, e.g. methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl or n-eicosyl, preferably methyl, ethyl, isopropyl, tert-butyl or amyl; (C3-C20)cycloalkyl, e.g. cyclopropyl, cyclobutyl, cyclopentyl, cyclohexyl, cycloheptyl or adamantyl; (C6-C30)aryl (C1-C20) alkyl, e.g. benzyl, 2-methylphenylmethyl, 3-methylphenylmethyl, 4-methylphenylmethyl, 2,3-dimethylphenylmethyl, 2,4-dimethylphenylmethyl, 2,5-dimethylphenylmethyl, 2,6-dimethylphenylmethyl, 3,4-dimethylphenylmethyl, 4,6-dimethylphenylmethyl, 2,3,4-trimethylphenylmethyl, 2,3,5-trimethylphenylmethyl, 2,3,6-trimethylphenylmethyl, 3,4,5-trimethylphenylmethyl, 2,4,6-trimethylphenylmethyl, 2,3,4,5-tetramethylphenylmethyl, 2,3,4,6-tetramethylphenylmethyl, 2,3,5,6-tetramethylphenylmethyl, pentamethylphenylmethyl, ethylphenylmethyl, n-propylphenylmethyl, isopropylphenylmethyl, n-butylphenylmethyl, sec-butylphenylmethyl, tert-butylphenylmethyl, n-pentylphenylmethyl, neopentylphenylmethyl, n-hexylphenylmethyl, n-octylphenylmethyl, n-decylphenylmethyl, n-dodecylphenylmethyl, n-tetradecylphenylmethyl, naphthylmethyl or anthracenylmethyl, preferably benzyl; (C1-C20) alkoxy, e.g. methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy or n-eicosoxy, preferably methoxy, ethoxy, isopropoxy or tert-butoxy; (C3-C20)alkylsiloxy, e.g. trimethylsiloxy, triethylsiloxy, tri-n-propylsiloxy, triisopropylsiloxy, tri-n-butylsiloxy, tri-sec-butylsiloxy, tri-tert-butylsiloxy, triisobutylsiloxy, tert-butyldimethylsiloxy, tri-n-pentylsiloxy, tri-n-hexylsiloxy or tricyclohexylsiloxy, preferably trimethylsiloxy or tert-butyldimethylsiloxy; (C1-C20)alkyl-substituted or (C6-C30) aryl-substituted amino, e.g. dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bistrimethylsilylamino or bis-tert-butyldimethylsilylamino; (C1-C20)alkyl-substituted or (C6-C30)aryl-substituted phosphine, e.g. dimethylphosphine, diethylphosphine, di-n-propylphosphine, diisopropylphosphine, di-n-butylphosphine, di-sec-butylphosphine, di-tert-butylphosphine, diisobutylphosphine, tert-butylisopropylphosphine, di-n-hexylphosphine, di-n-octylphosphine, di-n-decylphosphine, diphenylphosphine, dibenzylphosphine, methylethylphosphine, methylphenylphosphine, benzylhexylphosphine, bistrimethylsilylphosphine or bis-tert-butyldimethylsilylphosphine, preferably dimethylphosphine, diethylphosphine or diphenylphosphine; or (C1-C20)alkyl-substituted mercapto, e.g. methylmercaptan, ethylmercaptan, propylmercaptan, isopropylmercaptan, 1-butylmercaptan or isopentylmercaptan, preferably ethylmercaptan or isopropylmercaptan.

The transition metal complex represented by Chemical Formula 1 may be used along with an aluminoxane compound, a boron compound or a mixture thereof as cocatalyst for the preparation of an ethylene homopolymer or a copolymer of ethylene and α-olefin, which can extract the X ligand from the transition metal complex to make the center metal as cation, i.e. to act as counterion, or anion, having a weak binding force. The catalyst composition comprising the transition metal complex and the cocatalyst is also covered by the present invention.

The boron compound that can be used in the present invention as the cocatalyst may be one disclosed in U.S. Pat. No.

5,198,401 and may be selected from the compounds represented by the following Chemical Formulas 2~4:

(2)

(3)

(4)

where B is boron; $R^5$ is phenyl, which may be substituted by 3-5 substituents selected from fluorine, (C1-C20)alkyl substituted or unsubstituted by fluorine and (C1-C20)alkoxy substituted or unsubstituted by fluorine; $R^6$ is (C5-C7) aromatic radical, (C1-C20)alkyl (C6-C20)aryl radical or (C6-C30)aryl (C1-C20)alkyl radical, e.g. triphenylmethyl radical; Z is nitrogen or phosphorus; $R^7$ is $C1-C_{20}$ alkyl radical or anilinium radical substituted by two nitrogens and two (C1-C4)alkyl groups; and q is an integer 2 or 3.

Preferred examples of the boron-based cocatalyst include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl)borate, tetrakis(3,4,5-tetrafluorophenyl)borate, tetrakis(2,2,4-trifluorophenyl)borate, phenylbis(pentafluorophenyl)borate and tetrakis(3,5-bistrifluoromethylphenyl)borate. And, specific examples of the complex thereof include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, triphenylmethyl tetrakis(3,5-bistrifluoromethylphenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate and tri(dimethylphenyl)phosphonium tetrakis(pentafluorophenyl)borate. The most preferred among them are N,N-dimethylanilinium tetrakispentafluorophenyl borate, triphenylmethyl tetrakispentafluorophenyl borate or tris(pentafluorophenyl)borane.

The aluminum compound used in the present invention may be an aluminoxane compound represented by the following Chemical Formula 5 or 6, an organoaluminum compound represented by the following Chemical Formula 7, or an organoaluminum hydrocarbyl oxide compound represented by the following Chemical Formula 8 or Chemical Formula 9:

(5)

(6)

(7)

(8)

(9)

where $R^8$ is (C1-C20)alkyl, preferably methyl or isobutyl; m and q are integers from 5 to 20; $R^9$ and $R^{10}$ are (C1-C20) alkyl; E is hydrogen or halogen; r is an integer from 1 to 3; and $R^{11}$ is (C1-C20)alkyl or (C6-C30)aryl.

As specific examples of the aluminum compound, the aluminoxane compound may be methylaluminoxane, modified methylaluminoxane or tetraisobutylaluminoxane; the organoaluminum compound may be a trialkylaluminum, e.g. trimethylaluminum, triethylaluminum, tripropylaluminum, triisobutylaluminum or trihexylaluminum; a dialkylaluminum chloride, e.g. dimethylaluminum chloride, diethylaluminum chloride, dipropylaluminum chloride, diisobutylaluminum chloride or dihexylaluminum chloride; an alkylaluminum dichloride, e.g. methylaluminum dichloride, ethylaluminum dichloride, propylaluminum dichloride, isobutylaluminum dichloride or hexylaluminum dichloride; or a dialkylaluminum hydride, e.g. dimethylaluminum hydride, diethylaluminum hydride, dipropylaluminum hydride, diisobutylaluminum hydride or dihexylaluminum hydride, preferably a trialkylaluminum, more preferably triethylaluminum or triisobutylaluminum.

In the transition metal catalyst composition for the preparation of an ethylene homopolymer or a copolymer of ethylene and α-olefin according to the present invention, the molar proportion of the transition metal complex and the cocatalyst is center metal: boron:aluminum is 1:0.1-100:10-1,000, more preferably 1:0.5-5:25-500.

In another aspect, the present invention provides a process for preparing an ethylene homopolymer or a copolymer of ethylene and α-olefin using the transition metal catalyst composition is performed by contacting the transition metal catalyst and the cocatalyst with ethylene monomer or, if necessary, vinylic comonomer in the presence of an adequate organic solvent. The transition metal catalyst and the cocatalyst may be added separately into a reactor or may be previously mixed and added into a reactor. The sequence of addition or mixing condition, including temperature, concentration, etc., is not particularly limited.

Preferably, the organic solvent that may be used in the preparation process is a (C3-C20) hydrocarbon. Specific examples may include butane, isobutane, pentane, hexane, heptane, octane, isooctane, nonane, decane, dodecane, cyclohexane, methylcyclohexane, benzene, toluene, xylene, and the like.

Specifically, in the preparation of an ethylene homopolymer, ethylene is used as monomer alone. Preferred pressure of ethylene is 1-1,000 atm, more preferably 10-150 atm. And, preferred polymerization temperature is 60-300° C., more preferably 80-250° C.

And, in the preparation of a copolymer of ethylene and α-olefin, (C3-C18) α-olefin may be used as comonomer together with ethylene. Preferably, one selected from the group consisting of propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-octadecene and 1-eicosene may be used. More preferably, 1-butene, 1-hexene, 1-octene or 1-decene may be copolymerized with ethylene. In this case, preferred pressure of ethylene and preferred polymerization temperature are the same as for the preparation of the ethylene homopolymer. Typically, the ethylene copolymer prepared in accordance with the present invention comprises 50 weight % or more of ethylene, preferably 60 weight % or more, more preferably 60-99 weight % of ethylene.

As described earlier, the linear low density polyethylene (LLDPE) prepared using (C4-C10) α-olefin as comonomer has a density of 0.910-0.940 g/cc and a very or ultra low density polyethylene (VLDPE or ULDPE) having a density of 0.910 g/cc or lower or an olefin elastomer can be prepared. Further, in the preparation of an ethylene homopolymer or copolymer in accordance with the present invention, hydrogen may be used for the control of molecular weight. Typically, the homopolymer or copolymer has a weight average molecular weight ($M_w$) of 80,000-500,000.

Since the catalyst composition presented by the present invention exists in homogeneous state in a polymerization reactor, it can be applied for a solution polymerization process which is carried out at a temperature above the melting point of the corresponding polymer. It may also be applied to a slurry polymerization or gas phase polymerization process, as disclosed in U.S. Pat. No. 4,752,597, by supporting the transition metal complex catalyst and the cocatalyst on a porous metal oxide support as non-homogeneous catalyst composition.

The transition metal complex according to the present invention or the catalyst composition comprising the same can be prepared economically through a simple synthesis procedure. Further, because the catalyst maintains catalytic activity even at high temperature due to superior thermal stability, provides good copolymerization reactivity for olefins, and is capable of preparing high molecular weight polymers in high yield, it is commercially more applicable than previously known metallocene- and non-metallocene-based single site catalysts. Accordingly, it is useful in the preparation of ethylene homopolymers or copolymers of ethylene and α-olefin having various physical properties.

EXAMPLES

The following examples further illustrate the present invention, but are not intended to limit the same.

Unless specified otherwise, all the syntheses of ligands and catalysts were carried out under nitrogen atmosphere using standard Schlenk or glove box techniques. The organic solvent used for the reaction was subjected to reflux in the presence of sodium metal and benzophenone to remove water and distilled immediately before use. $^1$H-NMR analysis of the synthesized ligands and catalysts was carried out at room temperature using the Varian Oxford 300 MHz.

The polymerization solvent n-heptane was passed through a column packed with molecular sieve 5A and activated alumina and subjected to bubbling using high-purity nitrogen prior to use, in order to sufficiently remove water, oxygen or other catalytic poisons. The synthesized polymer was analyzed as follows.

1. Melt index (MI)

Measured in accordance with ASTM D 2839.

2. Density

Measured in accordance with ASTM D 1505 using a density gradient column.

3. Melting point ($T_m$)

Measured under nitrogen atmosphere at a rate of 10° C./min under the $2^{nd}$ heating condition using Dupont DSC2910.

4. Molecular weight and molecular weight distribution

Measured in 1,2,3-trichlorobenzene solvent at 135° C. at a rate of 1.0 mL/min using PL Mixed-BX2+preCol installed PL210 GPC. Molecular weight was corrected using PL polystyrene as standard material.

5. α-Olefin content (weight %) in copolymer

Measured at 120° C. at 125 MHz in $^{13}$C-NMR mode, using the Bruker DRX500 NMR (nuclear magnetic resonance) spectrometer and using a mixture solvent of 1,2,4-trichlorobenzene/$C_6D_6$ (7/3, wt/wt) [Randal, J. C. *JMS-Rev. Macromol. Chem. Phys.* 1980, C29, 201].

Preparation Example 1

Synthesis of 2,3-dihydro-2,2-dimethyl-7-benzofuranoxypentamethylcyclopentadienyl)titanium(IV) dichloride 2,3-Dihydro-2,2-dimethyl-7-benzofuranol (1.35 g, 5.5 mmol) was dissolved in 100 mL of n-hexane. n-Butyllithium (2.5 M hexane solution, 2.6 mL) was slowly added at −78° C. and stirring was carried out for 3 hours at room temperature. After the completion of reaction followed by the removal of hexane, white solid obtained by washing with hexane was dissolved in 50 mL of toluene. After slowly adding pentamethylcyclopentadienyltitanium(IV) trichloride (0.56 g, 2.0 mmol) dissolved in 5 mL of toluene dropwise at −78° C., reaction was carried out at room temperature for 12 hours. When the reaction was completed, volatile components were removed by filtering with celite. After recrystallization at −35° C. using purified toluene and hexane followed by filtration and drying under reduced pressure, 0.38 g of red solid was obtained.

Yield: 48%, $^1$H-NMR ($C_6D_6$) δ =1.16 (s, 6H), 2.02 (s, 15H), 2.54 (s, 2H), 6.54-6.59 (m, 2H), 7.01-7.13 (m, 1H) ppm.

Mass (APCI mode, m/z): 417.

Example 1

Ethylene polymerization was carried out as follows using a batch polymerization reactor. 97 mL of cyclohexane was put in a 200 mL stainless steel reactor sufficiently dried and substituted with nitrogen. Subsequently, 4.12 mL of modified methylaluminoxane-7 (modified MAO-7, Akzo-Nobel, 7 wt % Al Isopar solution) 36.4 mM toluene solution was added. After heating the reactor to 140° C., 1.192 mL of 2,3-dihydro-2,2-dimethyl-7-benzofuranoxypentamethylcyclopentadienyltitanium(IV) dichloride (1 mM toluene solution) synthesized in Preparation Example 1 and 0.65 mL of triphenylmethyliniumtetrakispentafluorophenyl borate (99%, Boulder Scientific) 4.65 mM toluene solution were sequentially added. Then, ethylene was filled up to a pressure of 30 kg/cm$^2$ and provided continuously for polymerization. Within 3 minutes of reaction, the temperature reached the maximum 188° C. 10 minutes later, 10 mL of ethanol (10 vol % HCl solution) was added to terminate the polymerization. After stirring for 4 hours using 1,500 mL of ethanol, the reaction product was filtered and separated. The collected reaction product was dried in a vacuum oven of 60° C. for 8 hours. 5.28 g of polymer was obtained. It was impossible to measure the melt index of the polymer. Upon analysis by gel chromatography, the polymer had a weight average molecular weight ($M_w$) of 440,000 g/mol and a molecular weight distribution ($M_w/M_n$) of 3.03.

Example 2

Copolymerization of ethylene and 1-octene was carried out as follows using a batch polymerization reactor. 88 mL of cyclohexane and 5 mL of 1-octene were put in a 200 mL stainless steel reactor sufficiently dried and substituted with nitrogen. Subsequently, 8.24 mL of modified MAO-7 (Akzo-Nobel, 7 wt % Al Isopar solution) 36.4 mM toluene solution was added. After heating the reactor to 145° C., 1.19 mL of 2,3-dihydro-2,2-dimethyl-7-benzofuranoxypentamethylcyclopentadienyltitanium(IV) dichloride (0.84 mM toluene solution) synthesized in Preparation Example 1 and 0.65 mL of triphenylmethyliniumtetrakispentafluorophenyl borate (99%, Boulder Scientific) 4.65 mM toluene solution were sequentially added. Then, ethylene was filled up to a pressure of 30 kg/cm² and provided continuously for polymerization. Within 1 minute of reaction, the temperature reached the maximum 169.6° C. 1 minute later, 10 mL of ethanol (10 vol % HCl solution) was added to terminate the polymerization. After stirring for 1 hour using 1,500 mL of ethanol, the reaction product was filtered and separated. The collected reaction product was dried in a vacuum oven of 60° C. for 8 hours. 3.92 g of polymer was obtained. The polymer had a melting point of 111.1° C., a melt index of 0.043 and a density of 0.9135 g/cc. Upon analysis by gel chromatography, the polymer had a weight average molecular weight of 186,500 g/mol and a molecular weight distribution of 2.66. 1-Octene content was 9.3 weight %.

Example 3

Copolymerization of ethylene and 1-octene was carried out as follows using a batch polymerization reactor. 83 mL of cyclohexane and 10 mL of 1-octene were put in a 200 mL stainless steel reactor sufficiently dried and substituted with nitrogen. Subsequently, 8.24 mL of modified MAO-7 (Akzo-Nobel, 7 wt % Al Isopar solution) 36.4 mM toluene solution was added. After heating the reactor to 142.6° C., 1.19 mL of 2,3-dihydro-2,2-dimethyl-7-benzofuranoxypentamethylcyclopentadienyltitanium(IV) dichloride (0.84 mM toluene solution) synthesized in Preparation Example 1 and 0.65 mL of triphenylmethyliniumtetrakispentafluorophenyl borate (99%, Boulder Scientific) 4.65 mM toluene solution were sequentially added. Then, ethylene was filled up to a pressure of 30 kg/cm² and provided continuously for polymerization. Within 1 minute of reaction, the temperature reached the maximum 168.2° C. 1 minute later, 10 mL of ethanol (10 vol % HCl solution) was added to terminate the polymerization. After stirring for 4 hours using 1,500 mL of ethanol, the reaction product was filtered and separated. The collected reaction product was dried in a vacuum oven of 60° C. for 8 hours. 3.82 g of polymer was obtained. The polymer had a melting point of 102.2° C., a melt index of 0.327 and a density of 0.9056 g/cc. Upon analysis by gel chromatography, the polymer had a weight average molecular weight of 131,700 g/mol and a molecular weight distribution of 2.92. 1-Octene content was 12.9 weight %.

The following Table 1 summarizes the result of homopolymerization of ethylene and copolymerization of ethylene and 1-octene using a batch-type stainless steel reactor.

TABLE 1

| | Polymerization temperature, initial (° C.) | Polymer (g) | Melt index (g/10 min) | Density (g/cc) | $M_w$ (g/mol) | $M_w/M_n$ |
|---|---|---|---|---|---|---|
| Ex. 1 | 140.0 | 5.28 | Immeasurable | — | 440,000 | 3.03 |
| Ex. 2 | 145.0 | 3.92 | 0.043 | 0.9135 | 186,500 | 2.66 |
| Ex. 3 | 142.6 | 3.82 | 0.324 | 0.9056 | 131,700 | 2.92 |

As can be seen from Table 1, even under high temperature condition (140° C. or above), high molecular weight polymers having narrow molecular weight distributions could be prepared (Examples 1-3). Especially, low density copolymers could be obtained successfully by increasing the 1-octent content (Examples 2 and 3).

The present invention has been described in detail with reference to example embodiments thereof. However, it will be appreciated by those skilled in the art that changed may be made in these embodiments without departing from the principles and spirit of the invention, the scope of which is defined in the accompanying claims and their equivalents.

What is claimed is:

1. A transition metal complex represented by the following Chemical Formula 1:

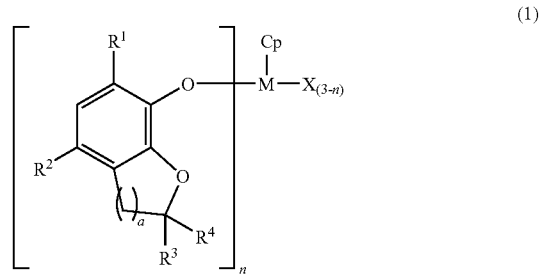

(1)

where

M is a group IV transition metal;

Cp is a cyclopentadienyl ring or a fused ring including a cyclopentadienyl ring which is capable of forming a $\eta^5$-bonding with M, wherein the cyclopentadienyl ring or the cyclopentadienyl fused ring may be substituted by (C1-C20)alkyl, (C6-C30) aryl, (C2-C20)alkenyl or (C6-C30)aryl (C1-C20)alkyl;

$R^1$ and $R^2$ are independently hydrogen, (C1-C20)alkyl, (C3-C20)cycloalkyl, (C6-C30)aryl, (C1-C20)alkyl (C6-C30)aryl, (C1-C20)alkyl-substituted or (C6-C30) aryl-substituted silyl, (C6-C30)aryl (C1-C10)alkyl, (C1-C20)alkoxy, (C1-C20)alkyl-substituted or (C6-C20) aryl-substituted siloxy, (C1-C20)alkyl-substituted or (C6-C30) aryl-substituted amino, (C1-C20)alkyl-substituted or (C6-C30)aryl-substituted phosphine, (C1-C20)alkyl-substituted mercapto, or nitro;

$R^3$ and $R^4$ are independently hydrogen, (C1-C20)alkyl, (C3-C20)cycloalkyl, (C6-C30)aryl, (C1-C20)alkyl (C6-C30)aryl, or (C6-C30)aryl (C1-C20)alkyl;

a is an integer 1 or 2;

n is an integer from 1 to 3; and

X is independently halogen, (C1-C20)alkyl, (C3-C20)cycloalkyl, (C6-C30)aryl (C1-C20)alkyl, (C1-C20) alkoxy, (C3-C20)alkylsiloxy, (C1-C20)alkyl-substituted or (C6-C30)aryl-substituted amino, (C1-C20) alkyl-substituted or (C6-C30) aryl-substituted phosphine, or (C1-C20)alkyl-substituted mercapto.

2. The transition metal complex according to claim 1, wherein M is titanium, zirconium or hafnium 3. The transition metal complex according to claim 1, wherein Cp is cyclopentadienyl or pentamethylcyclopentadienyl.

4. The transition metal complex according to claim 1, wherein n is 1 or 2.

5. The transition metal complex according to claim 1, wherein X is chlorine, methyl, methoxy, isopropoxy or dimethylamino.

6. A transition metal catalyst composition for the preparation of an ethylene homopolymer or a copolymer of ethylene and α-olefin comprising:

a transition metal complex according to claim 1; and an alkylaluminoxane or organoaluminum cocatalyst, a boron compound cocatalyst or a mixture thereof.

7. The transition metal catalyst composition for the preparation of an ethylene homopolymer or a copolymer of ethylene and α-olefin according to claim 6, wherein the alkylaluminoxane or organoaluminum cocatalyst is selected from methylaluminoxane, modified methylaluminoxane, tetraisobutylaluminoxane, trialkylaluminum, trimethylaluminum, triisobutylaluminum and a mixture thereof.

8. The transition metal catalyst composition for the preparation of an ethylene homopolymer or a copolymer of ethylene and α-olefin according to claim 6, wherein the proportion of the transition metal to the cocatalyst is 1:50 to 1:5,000 based on the molar ratio of transition metal M):aluminum.

9. The transition metal catalyst composition for the preparation of an ethylene homopolymer or a copolymer of ethylene and α-olefin according to claim 6, wherein the boron compound cocatalyst is selected from N,N-dimethylanilinium tetrakispentafluorophenyl borate, triphenylmethylinium tetrakispentafluorophenyl borate and a mixture thereof.

10. The transition metal catalyst composition for the preparation of an ethylene homopolymer or a copolymer of ethylene and α-olefin according to claim 6, wherein the proportion of the transition metal to the cocatalyst is 1:0.5-5:10-500 based on the molar ratio of transition metal (M):boron:aluminum.

11. A process for preparing an ethylene homopolymer or a copolymer of ethylene and α-olefin using the transition metal catalyst composition according to claim 6, wherein a comonomer polymerized with the ethylene is at least one selected from propylene, 1-butene, 1-pentene, 1-hexene, 1-heptene, 1-octene, 1-decene, 1-undecene, 1-dodecene, 1-tetradecene, 1-hexadecene and 1-eicosene, and the ethylene content in the copolymer of ethylene and α-olefin is 60-99 weight %.

12. The process for preparing an ethylene homopolymer or a copolymer of ethylene and α-olefin according to claim 11, wherein a polymerization is carried out in a reactor at a pressure of 6-150 atm and at a polymerization temperature of 60-250° C.

13. An ethylene homopolymer or a copolymer of ethylene and α-olefin prepared using the transition metal complex according to claim 1 as catalyst.

14. An ethylene homopolymer or a copolymer of ethylene and α-olefin prepared using the transition metal catalyst composition according to claim 6.

* * * * *